United States Patent [19]
Conti et al.

[11] Patent Number: 6,110,471
[45] Date of Patent: Aug. 29, 2000

[54] NON-HORMONAL METHOD OF CONTRACEPTION

[75] Inventors: Marco Conti; Aaron J. W. Hsueh, both of Stanford, Calif.; Alexander Tsafriri, Rehovot, Israel

[73] Assignee: The Board of Trustees of the Leland Stanford Junior University, Stanford, Calif.

[21] Appl. No.: 08/928,805

[22] Filed: Sep. 12, 1997

Related U.S. Application Data

[60] Provisional application No. 60/026,090, Sep. 13, 1996.

[51] Int. Cl.[7] ............................... A61K 9/00; A61F 6/06; A61F 13/00
[52] U.S. Cl. .................... 424/400; 424/422; 424/430; 424/439; 424/464; 514/841; 514/843
[58] Field of Search ..................... 424/400, 422, 424/430, 439, 464; 514/841, 843

[56] References Cited

U.S. PATENT DOCUMENTS

| | | | |
|---|---|---|---|
| 4,006,227 | 2/1977 | Gallegos et al. | 424/195 |
| 4,888,350 | 12/1989 | Omodei-Sale' | 514/384 |
| 5,110,925 | 5/1992 | Kusase et al. | 544/234 |
| 5,116,619 | 5/1992 | Greco et al. | 424/433 |
| 5,276,017 | 1/1994 | Feinberg et al. | 424/422 |
| 5,552,267 | 9/1996 | Stern et al. | 435/1.1 |

OTHER PUBLICATIONS

Tsafriri et al, Endocrinology Scoiety, Washington, DC., Abstract P1–153, Jun. 14–17, 1995.
Alvarez, R., et al., "Activation and Selective Inhibition of a Cyclic AMP–Specific Phosphodiesterase, PDE–4D3," Molecular Pharmacology. 48:616–622 (1995).
Conti, M., et al., "Recent Progress in Understanding the Hormonal Regulation of Phosphodiesterases," Endocr. Rev. 16(3):370–389 (1995).
Downs, S.M., and Hunzicker–Dunn, M., "Differential Regulation of Oocyte Maturation and Cumulus Expansion in the Mouse Oocyte–Cumulus Cell Complex by Site–Selective Analogs of Cyclic Adenosine Monophosphate," Dev. Biol. 172:72–85 (1995).
Maller, J.L., "Regulation of Amphibian Oocyte Maturation," Cell. Differ. 16:211–221 (1985).
Reinhardt, R.R., et al., "Distinctive Anatomical Patterns of Gene Expression for cGMP–inhibited Cyclic Nucleotide Phosphodiesterases," J. Clin. Invest. 95:1528–1538 (1995).
Sadler, S.E., "Inhibitors of Phosphodiesterase III Block Stimulation of *Xenopus laevis* Oocyte Ribosomal S6 Kinase Activity by Insulin–Like Growth Factor–I," Mol. Endocr. 5(12):1947–1954 (1991a).
Sadler, S.E., "Type III Phosphodiesterase Plays a Necessary Role in the Growth–Promoting Actions of Insulin, Insulin––Like Growth Factor–I, and Ha p21ras in *Xenopus laevis* Oocytes," Mol. Endocr. 5(12):1939–1946 (1991b).
Tsafriri, A., and Dekel, N., "Molecular Mechanisms in Ovulation," in *Molecular Biology of the Female Reproductive System* (Findlay, J.D., Ed.), pp. 207–258, Academic Press, San Diego (1994).
Tsafriri, A. and Conti, M., "Differential Inhibition of Phosphodiesterases in the Somatic and Oocyte Compartmens of Rat Follicles: Involvement in Oocyte Maturation," Endocrine Society, 77th Annual Meeting, Washington D.C. (Poster Sessions, P1–153, p. 151) Jun. 14–17, (1995).
Tsafriri, A., et al., "Oocyte Maturation Involves Compartmentalization and Opposing Changes of cAMP Levels in Follicular Somatic and Germ Cells: Studies Using Selective Phosphodiesterase Inhibitors," Dev. Biol. 178: 393–402 (1996).

*Primary Examiner*—Gollamudi S. Kishore
*Assistant Examiner*—Lakshmi Channavajjala
*Attorney, Agent, or Firm*—Charles K. Sholtz; Carol A. Stratford; Judy M. Mohr

[57] ABSTRACT

A method of contraception by delivering to the ovaries of a female mammal a pharmaceutically-effective dose of a PDE3-specific inhibitor at about the time of ovulation.

15 Claims, 8 Drawing Sheets

| Inhibitor/Type PDE | Oocyte cumulus complex or denuded oocyte | | Follicle-enclosed oocyte | | Two step culture: (18hr hCG or inhibitor -> 6hr control) |
|---|---|---|---|---|---|
| | Control | hCG | Control | hCG | |
| Control | + | – | – | + | – |
| MIX/Unspecific | – | ND | ND | – | + |
| Rolipram/4 | + | + | + | + | ND |
| Milrinone/3 Cilostamide/3 | – | – | – | – | – |

–:Immature oocytes, germinal vesicle intact;
+:Germinal vesicle breakdown; GVBD

| # | -Y- | $R_1$ | $R_2$ | $R_3$ | $R_4$ | $R_5$ | Physical Properties ( ) m.p. °C | phosphodiesterase inhibition $IC_{50}$ (μM) | | |
|---|---|---|---|---|---|---|---|---|---|---|
| | | | | | | | | PDE-I | PDE-II | PDE-III |
| 1 | $CH_2$-$C(CH_3)_2$-$CH_2$- | H | H | H | H | H | (272-274) | 900 | 250 | 1.2 |
| 2 | —$CH_2CH_2$— | H | H | H | H | H | (360 up) | 1000 | 235 | 1.2 |
| 3 | —$CH_2CH_2CH_2$— | H | H | H | H | H | 252-254 | 210 | 180 | 0.47 |
| 4 | —$CH_2CH_2$— | $CH_3$ | H | H | H | H | (284-285) | 610 | 330 | 2.0 |
| 14 | —$CH_2CH_2$— | H | H | H | H | H | (300 up) | 310 | 260 | 0.88 |
| 15 | —$CH_2CH_2$— | $CH_2$- | H | H | H | H | (285-286) | >1000 | 940 | 0.59 |
| 24 | —$CH_2CH_2$— | H | H | H | —$OCH_2$- | H | (327) dec. | >100 | 100 | 4.1 |
| 26 | —$CH_2CH_2$— | $CH_3$ | H | H | —$OCH_2$- | H | 280-281.5 | >1000 | 100 | 2.3 |
| 35 | —$CH_2CH_2$— | H | H | H | —$CH_2CH_2$- | H | (300 up) | >100 | 49 | 1.6 |

NON-HORMONAL METHOD OF CONTRACEPTION

This application claims the benefit of U.S. Provisional application Ser. No. 60/026,090, filed Sep. 13, 1996, incorporated herein by reference in its entirety.

This work was supported in part by NIH grants HD20788 and HD31566. Accordingly, the United States Government has certain rights in this invention.

FIELD OF THE INVENTION

The present invention relates to methods of contraception. In particular, the invention relates to methods of contraception which prevent the oocyte from maturing.

REFERENCES

Alvarez, R., et al., *Mol. Pharmacol.* 29:554–560 (1986).
Beavo, J. A., and Reifsnyder, D. H., *Trends. Pharmacol. Sci.* 11:150–155 (1990).
Bentley, J. K., and Beavo, J. A., *Curr. Opin. Cell Biol.* 4:233–240 (1992).
Brunton, L. L., and Mayer, S. E., *J. Biol. Chem.* 254:9714–9720 (1979).
Carr, B. R. and J. D. Wilson, "Disorders of the Ovary and Female Reproductive Tract" in *HARRISON'S PRINCIPLES OF INTERNAL MEDICINE, 12TH ED.*, Wilson, J. D., et al., Eds., McGraw-Hill, New York (1991).
Cho, W. K., et al., *J. Exp. Zool.* 187:383–386 (1974).
Chun, S. Y., et al., *Endocrine Journal* 1:481–486 (1993).
Conti, M., et al., *Endocrinology* 110:1189–1196 (1982).
Conti, M., et al., *Endocrinology* 114:2361–2368 (1984).
Conti, M., et al., *Endocr. Rev.* 12:218–234 (1991).
Conti, M., et al., *Endocr. Rev.* 16:370–389 (1995).
Dekel, N., "Hormonal control of ovulation," in *BIOCHEMICAL ACTION OF HORMONES* (Litwack, G., Ed.), Vol. 13, pp. 57–90. Academic Press (1986).
Dekel, N., "Interaction between the oocyte and the granulosa cells in the preovulatory follicle," in *ENDOCRINOLOGY AND PHYSIOLOGY OF REPRODUCTION* (Armstrong, D. T., et al., Eds.), pp. 197–209. Plenum Press, New York (1987).
Dekel, N., et al., *Dev. Biol.* 86:356–362 (1981).
Dekel, N., et al., *Biol. Reprod.* 31:244–250 (1984).
Dekel, N., et al., *Mol. Cell. Endocrin.* 56:115–121 (1988).
Dekel, N., and Beers, W. H., *Proc. Nat. Acad. Sci. USA* 75:3469–3473 (1978).
Dekel, N., and Sherizly, I., *FEBS Lett.* 151:153–155 (1983).
Dekel, N., and Piontkewitz, Y., *Bulletin des Anatomistes* 75:51–53 (1991).
Downs, P. M., "Control of the resumption of meiotic maturation in mammalian oocytes," in *GAMETES-THE OOCYTE* (Grudzinskas, J. G., and Yovich, Y. L., Eds), pp 150–192, Cambridge University Press, Cambridge, UK (1995).
Downs, S. M., and Hunzicker-Dunn, M., *Dev. Biol.* 172:72–85 (1995).
Eppig, J. J., and Downs, S. M., *Biol. Reprod.* 30:1–12 (1984).
Hillensjo, T., et al., *J. Clin. Endocr. Metab.* 47:1332–1335 (1978a).
Hillensjo, T., et al., *Acta Endocr. Copenh.* 87:377–388 (1978b).
Hsueh, A. J. W., *Human Reproduction* 10:1997–2000 (1995).
Larsen, W. J., et al., *Devel. Biol.* 113:517–521 (1986).
Larsen, W. J., et al., *Dev Biol* 122:61–71 (1987).
Lindner, H. R., et al., *Rec. Progr. Horm. Res.* 30:79–138 (1974).
Meacci, E., et al., *Proc. Natl. Acad. Sci. USA* 89:3721–3725 (1992).
Michaeli, T., et al., *J. Biol. Chem.* 268:12925–12932 (1993).
Monaco, L., et al., *J. Biol. Chem.* 269:347–357 (1994).
Ott, L., in *AN INTRODUCTION TO DATA ANALYSIS*, pp 227–242, PWS-Kent Publishing, Boston, Mass. (1988).
Mullis, K. B., U.S. Pat. No. 4,683,202, issued Jul. 28, 1987.
Mullis, K. B., et al., U.S. Pat. No. 4,683,195, issued Jul. 28, 1987.
Nicolson, C. D., et al., *Trends Pharm. Sci.* 12:19–24 (1991).
Pincus, G., and Enzmann, E. V., *J. Exp. Med.* 62:655–675 (1935).
Piontkewitz, Y., and Dekel, N., *Endocrine Journal* 1:365–372 (1993).
Racowsky, C., et al., *Eur. J. Cell Biol.* 49:244–251 (1989).
Reinhardt, R. R., et al., *J. Clin. Invest.* 95:1528–1538 (1995).
Sadler, S. E., *Mol. Endocr.* 5:1947–1954 (1991a).
Sadler, S. E., and Maller, J. L., *J. Biol. Chem.* 262:10644–10650 (1987).
Sadler, S. E., and Maller, J. L., *J. Biol. Chem.* 264:856–861 (1989).
Schmidtke, J., et al., *Acta Endocrinol. (Copenh).* 95:404–413 (1990).
Schultz, R. M., "Molecular aspects of mammalian oocyte growth and maturation," in *EXPERIMENTAL APPROACHES TO MAMMALIAN EMBRYOGENIC DEVELOPMENT* (Rossant, J., and Pederson, R. A., Eds.), pp. 195–237, Cambridge University Press, Cambridge (1986).
Sherizly, I., et al., *Human Reprd.* 3:761–766 (1988).
Swinnen, J. V., et al., *Proc. Natl. Acad. Sci. USA* 86:8197–8201 (1989).
Swinnen, J. V., et al., *J. Biol. Chem.* 266:14383–14389 (1991).
Taira, M., et al., *J. Biol. Chem.* 268:18573–18579 (1993).
Tsafriri, A., "Oocyte maturation in mammals," in *THE VERTEBRATE OVARY* (Jones, R. E., Ed.), pp. 409–442, Plenum Press, New York, London (1978).
Tsafriri, A., et al., *J. Reprod. Fert.* 31:39–50 (1972).
Tsafriri, A., and Kraicer, P. F., *J. Reprod. Fert.* 29:387–393 (1972).
Tsafriri, A., and Dekel, N., "Molecular mechanisms in ovulation," in *MOLECULAR BIOLOGY OF THE FEMALE REPRODUCTIVE SYSTEM* (Findlay, J. D., Ed.), pp. 207–258, Academic Press, San Diego (1994).
Tsafriri, A. and Adashi, E. Y., "Local Nonsteroidal Regulators of Ovarian Function," in *THE PHYSIOLOGY OF REPRODUCTION* (Knobil, E. and Neill, J. D., Eds) pp. 817–860, Raven Press, New York (1996).
Vivarelli, E., et al., *Cell Differentiation* 12:271–276 (1983).
Yoshimura, Y., et al., *Endocrinology* 131:351–356 (1992a).
Yoshimura, Y., et al., *J. Reprod. Fert.* 95:803–812 (1992b).

BACKGROUND OF THE INVENTION

Current methods of fertility control include physical prevention of gamete interaction by barrier methods, spermicides, surgical methods, and hormonal disruption of the menstrual cycle using steroids (Hsueh, 1995). The latter strategy, commonly known as the steroid contraceptive pill, is one of the most widely used methods of contraception by women. Although of undisputed efficacy, the long term exposure to estrogen/progestogen that this method involves several undesirable side effects. These include a possible increase in the incidence of breast cancer and thrombosis, risks which have been the focus of concern and public debate. Accordingly, there exists a need for a safe, effective and reliable method of contraception that does not have the undesirable side effects associated with steroid contraceptives.

SUMMARY OF THE INVENTION

In one aspect, the present invention includes a method of contraception. The method includes delivering to the ovaries of a female mammal (e.g., a woman) a pharmaceutically-effective dose of a PDE3-specific inhibitor at the "midcycle" period in the female ovarian cycle (i.e., around the time of ovulation; preferably over a time period spanning about 12 hours before the LH surge to at least about 48 hours after the LH surge). In one embodiment, the PDE3-specific inhibitor is administered continuously so long as the female subjects is in need of contraception. In another embodiment, administration of the PDE3-specific inhibitor is initiated one week after start of the ovarian cycle (i.e., one week after initiation of menstrual flow), and is continued for two and one half weeks thereafter.

In a general embodiment, the PDE3-specific inhibitor is selected from the group consisting of milrinone, cilostamide, amrinone, enoximone, CI-930, anagrelide, pimobendan, siguazodan (SKF-94836), lixazinone (RS-82856), imazodan (CI-914), indolidan (LY195115), quazinone, SKF 94120, Org 30029, adibendan (BM 14,478), APP 201-533, carbazeran, cilostazole, E-1020, IPS-1251, nanterinone (UK-61260), pelrinone, RMI 82249, UD-CG 212, bemarinone (ORF-16,600), CK-2130, motapizone, OPC-3911, Ro 13-6438, sulmazole, vesnarinone (OPC-8212), buquineran, DPN 205-734, ICI-170777, isomazole (LY175326), MCl-154, MS-857, OPC-8490, piroximone (MDL 19205), RS-1893, saterinone, ZSY- 39, ICI 118233, and compounds 1, 2, 3, 4, 14, 15, 24, 26 and 35 of FIGS. 7A and 7B.

In a specific embodiment, the PDE3-specific inhibitor is cilostamide. In another embodiment, the PDE3-specific inhibitor is lixazinone. In yet another embodiment, the PDE3-specific inhibitor is indolidan.

The delivery may be, for example, via oral administration, vaginal administration, injection, implantable device or transdermal patch.

The dosage of the compound is generally between about 1 mg/kg and about 100 mg/kg per day, depending on the pharmacokinetics, bioavailability and activity of the particular compound selected.

In another aspect, the invention includes a contraceptive device for use in preventing oocyte maturation in a female mammal. The device includes a vaginal insert, and compound release means in the insert or cap for releasing a PDE3-specific inhibitor at a dose effective to prevent or inhibit oocyte maturation.

These and other objects and features of the invention will become more fully apparent when the following detailed description is read in conjunction with the accompanying drawings.

BRIEF DESCRIPTION OF THE SEQUENCES

Figure 1:
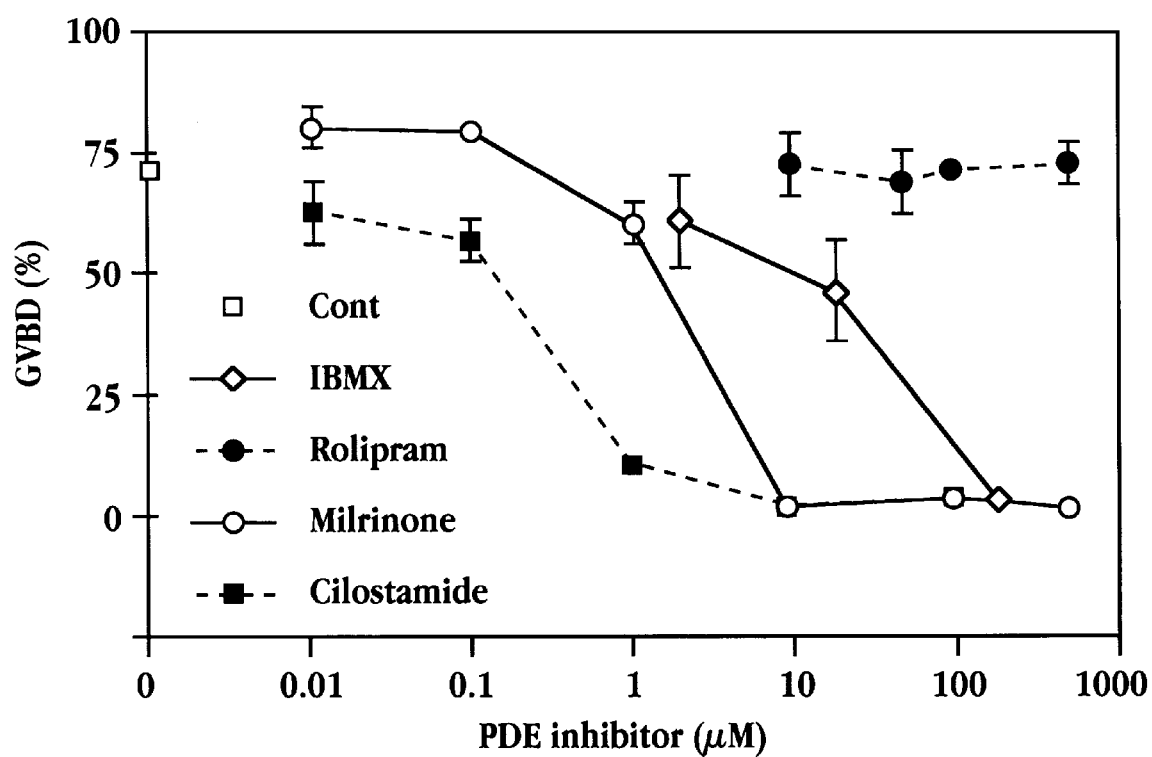
FIG. 1 shows a plot of the % GVBD (a measure of oocyte maturation) in isolated oocytes as a function of concentration of PDE inhibitors IBMX, milrinone, cilostamide, and rolipram.

SEQ ID NO:1 is the nucleotide sequence of Primer A, corresponding to bases 2598–2617 of rat PDE3A.

SEQ ID NO:2 is the nucleotide sequence of Primer B, complementary to bases 2949–2968 of rat PDE3A sequence.

SEQ ID NO:3 is the nucleotide sequence of Primer C, corresponding to bases 2310–2325 of the sequence of rat PDE3B.

SEQ ID NO:4 is the nucleotide sequence of Primer D, corresponding to bases 3343–3363 of the sequence of rat PDE3B.

DETAILED DESCRIPTION OF THE INVENTION

I. Definitions

The term "ovum" or "mature oocyte" refers to the mature female haploid egg cell which has matured from an oocyte by undergoing meiosis. The ovum is released at the time of ovulation from the follicles of the ovaries.

The term "ovulation" refers to the release by the follicles of one or more ova or mature oocytes. Ovulation is characterized in humans by specific hormonal changes; in particular, it occurs just subsequent to a surge in luteinizing hormone (LH) and follicle stimulating hormone (FSH) levels and a decrease in level of estrogen.

II. Overview of Invention

The present invention provides a non-hormonal method of contraception. The invention is based on the demonstration that the processes of oocyte maturation and ovulation can be uncoupled using inhibitors of type 3 phosphodiesterases (PDE3s), enzymes involved in signal transduction that are present in the oocyte but not in the somatic component of the ovary. According to the present invention, these compounds can be considered antifertility, or contraceptive agents. An advantage of this approach is the prevention of oocyte maturation and subsequent fertilization, without disruption of ovulation and of the normal menstrual cycle, thus maintaining the endogenous hormonal environment.

Experiments performed in support of the present invention have resolved an apparent paradox with respect to the role of cAMP in oocyte maturation. On one hand, it was known that a decrease in intra-oocyte levels of cAMP precedes germinal vesicle breakdown (GVBD). For example, in the mammalian system, isolated oocytes undergo spontaneous maturation in vitro, but this process is blocked by treatment with a phosphodiesterase (PDE) inhibitor, IBMX, which increases intra-oocyte cAMP levels.

In apparent contrast to these observations, however, the same inhibitor, when added to cultured follicles for a brief time, increases follicle cAMP levels, followed by the induction of GVBD.

Results of experiments performed in support of the present invention show that these apparently contradictory observations may be due to opposing fluctuations of cAMP levels in the somatic granulosa and germ cells caused by selective expression and regulation of distinct PDE isoforms in the somatic and germ cell compartments of the follicle.

III. Ovulation

For the purposes of the present discussion, the female reproductive system comprises the ovaries, Fallopian tubes or oviducts, uterus and vagina. Under influence of gonadotropins, a group of follicles, termed "primary follicles", is recruited. By day 6 of the menstrual cycle, one of these becomes mature or "dominant". This process is characterized by enlargement of the fluid-filled antrum and accelerated growth of the granulosa. The follicles not destined to ovulate begin degeneration, while the oocyte in the primary follicle is arrested at the prophase of meiosis (Carr and Wilson, 1991).

Just prior to the start of ovulation during the mid-cycle, a preovulatory increase in the gonadotropin LH triggers the final step of maturation (resumption of meiosis) of the oocyte (Tsafriri and Adashi 1996), followed by the rupture of the follicle wall to allow the mature oocyte to be released. A morphological expression of oocyte maturation is the dissolution of the germinal vesicle (germinal vesicle breakdown, GVBD). If final maturation of the oocyte is prevented, the oocyte cannot be fertilized by the spermatozoon. It has been demonstrated that high levels of the second messenger cAMP in the oocyte prevent this maturation.

IV. cAMP, Phosphodiesterases (PDEs) and PDE Inhibitors

Cellular steady state levels of cAMP are the result of a balance between the rate of synthesis (activity of adenylate cyclase), degradation by phosphodiesterases (PDEs) and extrusion from the cell. PDEs are thought to play an important role in the regulation of cellular cAMP levels (Brunton and Mayer, 1979). There is substantial evidence for the hormonal regulation of cellular PDE (reviewed by Conti, et al., 1991, 1995), including regulation in the Sertoli cells (Conti, et al., 1982), the ovary (Schmidtke, et al., 1980) and in the granulosa cells (Conti, et al., 1984). Furthermore, by transfecting a cDNA coding for a PDE into hormone responsive cells, it was demonstrated that even minor changes in the rate of cAMP degradation elicited a major impact on intracellular cAMP levels (Swinnen, et al., 1991).

The complexity of the PDE system has recently become apparent with the identification of a large family of PDE isoforms (Beavo and Reifsnyder, 1990; Conti, et al., 1991). The initial cloning of cAMP-specific PDEs (cAMP-PDE type 4) was followed by identifications of at least 25 different PDE forms in mammals. The PDEs were classified into 7 distinct families (types) on the basis of their kinetic characteristics, substrate specificity and regulation (Bentley and Beavo, 1992; Conti, et al., 1995; Michaeli, et al., 1993).

A further diversification appears within some of the different PDE types. For example, at least four type 4 PDE genes (mammalian homologues of the Drosophila melanogaster dunce PDE) are present in the rat, mouse and human. Since several mRNA variants were characterized, it appears that more than one protein is derived from each gene (Conti, et al., 1995; Monaco, et al., 1994). Likewise, cDNAs for two type 3 PDEs (cGMP-inhibited: CGI-PDE) have been cloned (Meacci, et al., 1992; Taira, et al., 1993). PDE3A mRNA is highly expressed in rat adipocytes, whereas PDE3B is highly expressed in rat cardiac tissue.

Until recently, the only inhibitors of PDEs were nonselective (inhibited all types of PDEs). However, a "second generation" of PDE inhibitors, selective for various families of PDEs, has now been developed (see Nicolson, et al., 1991, incorporated herein by reference). For example, rolipram inhibits the type 4 PDE with an $ED_{50}$ of 0.1–0.5 $\mu M$, and has an effect on the calmodulin stimulated PDEs only in the millimolar range. Similarly, the compounds milrinone and cilostamide are much more effective in suppressing the type 3 PDE than the type 4 PDE. Specifically, milrinone and cilostamide inhibit type 3 PDEs in the submicromolar range but affect type 4 PDEs only at about 100-fold higher concentrations.

According to the present invention, PDE3-specific inhibitors, as exemplified herein by milrinone and cilostamide, selectively inhibit type 3 PDEs at a concentration that is at least 10-fold lower than is required for a similar inhibitory effect on other types of PDEs, such as type IV PDEs. Preferably, the specific inhibition occurs at a concentration that is at least 50-fold lower than inhibition of such other types of PDEs.

Figures 7A, 7B:
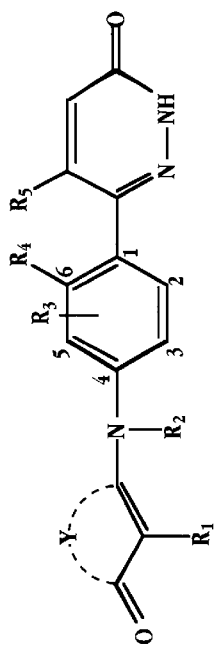
FIGS. 7A and 7B show the structures and biological activities of pyridazinone derivative PDE3-specific inhibitors.

Examples of PDE3-specific inhibitors include milrinone and cilostamide as described above, as well as amrinone, enoximone, CI-930, anagrelide, pimobendan, siguazodan (SKF-94836), lixazinone (RS-82856), imazodan (CI-914), indolidan (LY195115), quazinone, SKF 94120, Org 30029, adibendan (BM 14,478), APP 201-533, carbazeran, cilostazole, E-1020, IPS-1251, nanterinone (UK-61260), pelrinone, RMI 82249, UD-CG 212, bemarinone (ORF-16, 600), CK-2130, motapizone, OPC-3911, Ro 13-6438, sulmazole, vesnarinone (OPC-8212), buquineran, DPN 205-734, ICI-170777, isomazole (LY175326), MCI-154, MS-857, OPC-8490, piroximone (MDL 19205), RS-1893, saterinone, ZSY-39, and ICI 118233. Lixazinone (N-cyclohexyl-N-methyl-4-(7-oxy-1,2,3,5-tetrahydroimidazo[2,1-b]quinazolin-2-one) butyramide) and indolidan have a particularly high selectivity for type 3 PDE (Alvarez, et al., 1986). Other suitable PDE3-specific inhibitors include the pyridazinone derivative compounds shown in FIGS. 7A and 7B (compounds 1, 2, 3, 4, 14, 15, 24, 26 and 35). The synthesis of these compounds is described in U.S. Pat. No. 5,110,925, issued May 5, 1992, incorporated herein by reference. All other compounds described herein can be obtained from commercial manufacturers and/or synthesized according to methods known in the art. Table 1 provides references and manufacturer sources that will aid the practitioner in obtaining these compounds. All references cited are incorporated herein by reference.

TABLE 1

| Compound | Method of Preparation |
|---|---|
| Adibendan | Mertens, A. et al., J. Med. Chem. 30(8):1279–87 (1987); German Patent DE 3642315 (1988); Boehringer Mannheim GmbH, Germany |
| Indolindan | Robertson, D. W. et al., J. Med. Chem. 29(10):1832–40 (1986); Eli Lilly Co., Indianapolis, IN |
| Org 30029 N-hydroxy-5,6-dimethyl-benzo(b)thiophene-2-carboximidamide | Logan R. T. et al., European Patent No. EP 352832 (1990); AKZO N.V., Netherlands. |
| Saterinone | Stenzel, W. et al., European Patent No. EP 167121 (1986) |
| CK 2130 4-ethyl-1,3-dihydro-5-(4-(2-methyl-1H-imidazol-1-yl)benzoyl)- | Hagedorn, A. A. et al., J. Med. Chem. 30(8):1342–47 (1987) |

TABLE 1-continued

| Compound | Method of Preparation |
|---|---|
| 2H-imidazol-2-one | |
| Nanterinone | Alabaster, C. T. et al., J. Med. Chem. 32(3):575–83 (1989) |
| RS 1893 2-(2-chloro-4-(2,3,4,5-tetrahydro-3-oxo-6-pyridazinyl))-phenoxy-N-(2-(2-morpholinoethyl)-acetamide | Morisawa, Y. et al., European Patent No. EP 178189 (1986); Sankyo Co., Ltd., Japan |
| ZSY 39 4-methyl-5-(4-pyridinyl)-thiazole-2-carboxyamide | Takase, M. et al., European Patent No. EP 199968 (1986); Zenyaku Kogyo Co., Ltd., Japan |
| MS 857 7-(4-pyridyl)-5,6,7,8-tetrahydro-3(2H)-isoquinolinone | Kaiho, T. et al., J. Med. Chem. 32(2):351–57 (1989); Mitsui Toatsu Chem. Inc., Yokohama, Japan |
| UD-CG 212 2-(4-hydroxy-phenyl)-5-(5-methyl-3-oxo-4,5-dihydo-2H-6-puridazinyl) benzimidazole | Austel, V. et al., German Patent No. DE 3728244 (1989) |
| Siguazodan | Burpitt, B. E. et al., J. Heterocycl. Chem. 25(6):1689–95 (1988) |
| E 1020 loprinone | Yamanaka, M. et al., Chem. Pharm. Bull. 39(6):1556–67 (1991) |
| Buquineran | Danilewicz, J. C. et al., German Patent No. DE 2530894 (1976) Pfizer, Inc. |
| IPS 1251 | Cheshire, D. et al., PCT Application No. WO 9720815 (1997) Astra Pharmaceuticals, Ltd., UK |
| Amrinone | Gomez-Parra, V. et al., Arch. Pharm. (Weinheim, Cer.) 325(8):483–90 (1992) |
| Anagrelide | Reiter, J. et al;, U.S. Pat. No. 5,391,737 (1995); Roberts Pharmaceutical Corp.; Roberts Laboratories Inc., USA |
| Cilostamide | Lugnier, C. et al., Eur. J. Med. Chem.--Chim. Ther. 20(2):121–25 (1985) |
| RO 13-6438 (R-6-chloro-1,5-dihydro-3-methylimidazo -(2,1-b) quinazolin -2(3H)-one) | Stalder, H., Helv. Chim. Acta 69(8):1887–97 (1986); Hoffmann LaRoche; Basel, Switzerland |
| Carbazeran | Campbell, S. F. et al., United Kingdom Patent No. GB2000136 (1979); Pfizer Ltd., UK |
| Sulmazole | Sun, C. et al., J. Med. Coll. PLA 1(3):285–90 (1986) |
| Cilostazol | Nishi, T. et al., Chem. Pharm. Bull. 31(4):1151–57 (1983); Otsuka Pharm. Co., Ltd., Tokushima, Japan |
| Pimobendan | Dorsch, D. et al., Bioorg. Med. Chem. Lett. 4(11):1297–302 (1994) Merck, Darmstadt, Germany |
| OPC 3911 N-cyclohexyl-N-2-hydroxyethyl-4(6-(1-2-dihydro-2-oxoquinolyloxy)) butyramide | Nishi, T. et al., Chein. Pharin. Bull. 31(3):852–60 (1983); Otsuka Pharm Co., Ltd., Tokushima, Japan |
| RMI 82249 1,3-dihydro-4(4-methoxybenzoyl)-5-methyl-2H-imidazol-2-one | Grisar, J. M. et al., United Kingdom Patent No. GB 2097792 (1982) |
| Enoximone | Schnettler, R. A et al., U.S. Pat. No. 4,405,635 (1983) |
| APP 201-533 3-amino-6-methyl-5-phenyl-1,2-dihydropyrid-2-on | Bormann, G., French Patent No. FR 2477148 (1981); Sandoz, Switzerland |
| Imazodan | Sircar, I. et al., Eur. J. Med. Chem. 24(4):349–55 (1989); Warner-Lambert Co., Ann Arbor, MI |
| Piroximone | Schnettler, R. A. et al., J. Med. Chem. 29(5):860–62 (1986) |
| Isomazole | Goedde, J. A. et al., U.S. Pat. No. 4,740,599 (1988) |
| CI 930 3-(2H)-pyridazinone-4,5-dihydro-6-(4-(1H-imidazolyl) phenyl)-5-methyl monohydrochloride | Sircar, I. et al., Eur. J. Med. Chem. 24(4):349–55 (1989) |
| DPN 205-734 5-(4-cyanophenyl)-1,2-dihydro-6-methyl-2-oxopyridin-3-carbonitrile | Bormann, G., German Patent No. DE 3317289 (1983); Sandoz, Germany |
| SKF 94120 5-(4-acetamidophenyl)pyrazin-2(1H) | Ross, D. A. et al., Xenobiotica 18(12):1373–87 (1988); Smith-Kline |
| Motapizone | Hilboll, G. et al., German Patent No. DE 3241102 (1984) |
| Bemarinone | Conley, R. A. et al., J. Heterocycl. Chem. 32(3):761–70 (1995) |
| ICI 118233 6-(p-(3-methylureido)phenyl)-3(2H)-pyridazinone | Thyes, M. et al., German Patent No. DE 3302442 (1984); ICI Pharmaceuticals, UK |
| Lixazinone | Meanwell, N. A., et al., J. Med. Chem. 35(14):2672–87 (1992) |
| MCI 154 6-(4-(4-pyridyl)aminophenyl)-4,5-dihydro-3(2H)-pyridazinone | Okushima, H. et al., J. Med. Chem. 30(7):1157–61 (1987) |
| ICI 170777 (6RS)-6-methyl-5-(pyrid-4-yl)-3H,6H-1,3,4-thiadiazin-2-one | McKillop, D. et al., Xenobiotica 20(4):401–15 (1990); U.S. Pat. No. 4,558,045; ICI Pharmaceuticals, Great Britain. |
| OPC 8490 3,4-dihydro-6-(4-(4-oxo-4-phenylbutyl)-1-piperazinylcarbonyl)-2(1H)-quinolinone citrate | Furukawa, Y. et al., Jpn. Heart J. 30(3):387–98 (1989). (Produced by Otsuka America; Otsuka Chemical Co. Ltd., Japan) |
| Pelrinone | Bagli, J. et al., J. Med. Chem. 31(4):814–23 (1988) |
| Vesnarinone | Tominaga, M. et al., Chem. Pharm. Bull. 32(6):2100–10 (1984) |

V. Experimental Models of Oocyte Maturation

Two major in vitro models have been employed for investigating the control of meiotic maturation in mammalian oocytes. Pincus and Enzmann (1935) demonstrated that rabbit oocytes liberated from their follicles undergo spontaneous maturation in culture, without any need for hormonal stimulation. Such spontaneous maturation of oocytes cultured either denuded of their cumulus cells or within their cumulus complex was confirmed in all mammalian species examined (reviewed by Tsafriri, 1978) and has been widely employed for studying oocyte maturation. Spontaneous maturation of mouse oocytes in vitro when released from their follicles can be reversibly blocked by addition of a derivative of cAMP or a phosphodiesterase inhibitor (Cho, et al., 1974), a finding that has been confirmed in several mammalian species (Dekel and Beers, 1978; Eppig and Downs, 1984; Schultz, 1986).

In the second model, consisting of explanted preovulatory follicles, resumption of meiosis is dependent upon gonadotropin stimulation in vivo or in vitro (Tsafriri, et al., 1972), an effect that can be mimicked by other hormones (Tsafriri and Dekel, 1994). In contrast to the isolated oocyte model, treatment of follicle-enclosed oocytes with agents that increase cAMP also leads to the resumption of oocyte maturation (Hillensjo, et al., 1978b; Lindner, et al., 1974; Tsafriri, et al., 1972). Thus, GVBD is induced following: (i) injection of the cAMP derivative dibutyryl cAMP (dbcAMP) into the follicular antrum (Tsafriri, et al., 1972); (ii) transient exposure of follicles to 8-bromo-cAMP (Hillensjo, et al., 1978b), dbcAMP or isobutylmethylxanthine (IBMX) (Dekel, et al., 1981); and (iii) addition of forskolin to cultured follicle-enclosed oocytes (Dekel, 1986; Dekel and Sherizly, 1983; Yoshimura, et al., 1992a; Yoshimura, et al., 1992b). Although these findings suggest that LH-induced oocyte maturation is a cAMP-mediated response, continuous presence of membrane permeable cAMP derivatives or inhibitors of phosphodiesterase prevents the LH-stimulated oocyte maturation in explanted follicles (Dekel, et al., 1981; Hillensjo, et al., 1978a; Lindner, et al., 1974; Tsafriri, et al., 1972). The apparently opposing actions of cAMP in the two models present a paradox. A rise in follicular cAMP mediates LH action to induce oocyte maturation, while intraoocyte cAMP inhibits the process.

VI. Results

Experiments performed in support of the present invention and detailed below demonstrate that distinct types of phosphodiesterases may selectively control cAMP levels in the granulosa cells and in the oocyte, and thus participate in the regulation of oocyte maturation.

Specific inhibitors of type 3 and type 4 PDEs were tested in the experimental models described above. Example 1 details the effects of these inhibitors on spontaneous maturation of isolated oocytes obtained 48 hours after eCG-stimulation of immature rats. The results, shown in FIG. 1, illustrate that the spontaneous maturation of rat oocytes was blocked in a dose dependent manner by the non-specific PDE inhibitor IBMX, as well as by the type 3 PDE-specific inhibitors milrinone and cilostamide, but not by the type 4 PDE-specific inhibitor rolipram.

Example 2 describes the effects of the inhibitors on the maturation of follicle-enclosed oocytes, which mature only in response to hormonal stimuli. In this experimental model, LH treatment causes resumption of meiosis. The results, shown in FIGS. 2A and 2B, confirm the results with denuded oocytes. Specifically, the results demonstrate that IBMX, cilostamide and milrinone each blocked LH-induced maturation when present throughout the culture period. Treatment with increasing doses of rolipram did not inhibit the maturation of follicle-enclosed oocytes exposed to LH/hCG. However, in the absence of LH/hCG, rolipram stimulated the resumption of meiosis in follicles cultured without LH at doses between 0.05 and 5 $\mu$M.

In situ hybridization and PCR experiments, detailed in Example 3, determined that type 3 PDEs (PDE3) are expressed in the oocyte but not in granulosa cells (FIGS. 3A–F), while type 4 PDEs (PDE4) are expressed mostly in granulosa cells (FIGS. 4A–F).

Example 4 describes experiments on PDE3 inhibition of oocyte maturation in vivo. Cycling mice were treated daily with 100 mg/kg PDE3 inhibitors. Treated animals had estrous cycles similar to the controls and spontaneous ovulation took place at the appropriate time, indicating that granulosa cell function was not impaired by this in vivo treatment. However, morphological examination of the ovulated oocytes from treated animals indicated that maturation had not occurred and the germinal vesicle was still present. These experiments demonstrate that inhibition of PDE3 prevents meiotic maturation in vivo and causes the ovulation of immature and incompetent oocytes, and confirm that this approach can be used as a non-hormonal method of contraception.

In summary, the results of the experiments described in Examples 1, 2, 3 and 4 indicate that PDE3-specific inhibitors block the resumption of meiosis both in vitro (using two experimental models of oocyte maturation) and in vivo. The potency of cilostamide and milrinone in blocking GVBD correlates well with their potency in inhibiting PDE3 activity. The possibility that these inhibitors have toxic effects on the oocyte was ruled out by showing that the inhibitory effects are reversible. These results also confirm that there is a functional compartmentalization of the PDE in the follicle, that PDE3 activity is necessary for meiotic resumption in the oocyte, and that inhibition of PDE3 blocks resumption of meiosis both in denuded or follicle-enclosed oocytes. Because PDE3 inhibitors do not affect PDE4 present in granulosa cells, it is contemplated that the ovulatory process can be maintained even though oocyte maturation is blocked by PDE3 inhibitors.

Rolipram, at concentrations as high as 1 mM, did not affect the spontaneous maturation of isolated oocytes nor the maturation of follicle-enclosed oocytes triggered by hCG/LH, demonstrating that either a PDE4 is not expressed in oocytes at this stage of maturation or, if present, is largely inactive. However, treatment with rolipram by itself effectively stimulated the maturation of follicle-enclosed oocytes cultured without hCG/LH.

Figure 5:
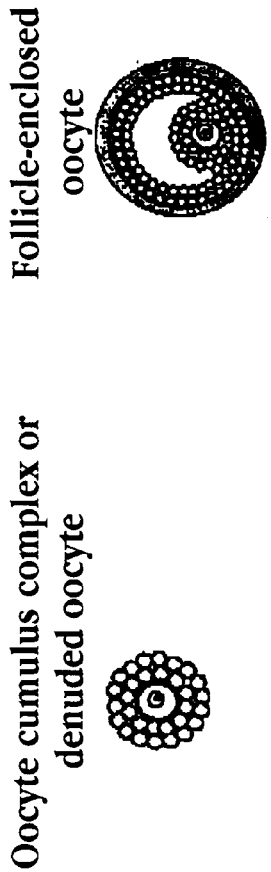
FIG. 5 shows a summary of the effects of PDE inhibitors on the maturation of isolated and follicle-enclosed oocytes.
Figure 6A:
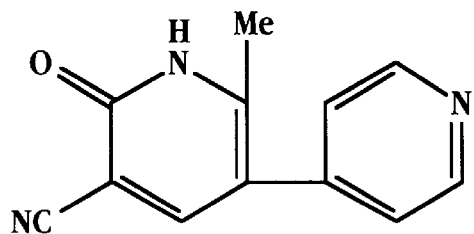
FIG. 6A shows the structure of milrinone.
Figure 6B:
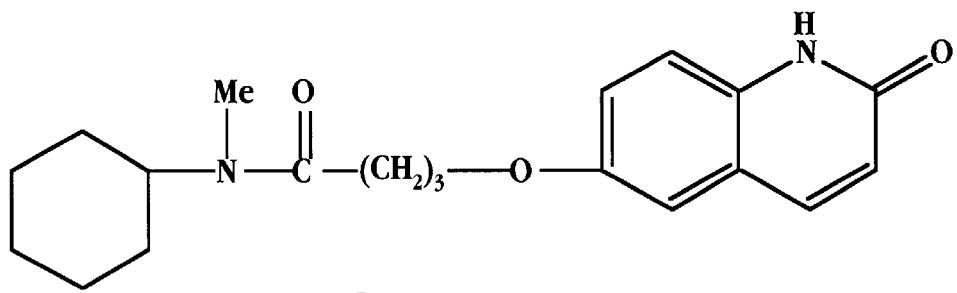
FIG. 6B shows the structure of cilostamide.
Figure 6C:
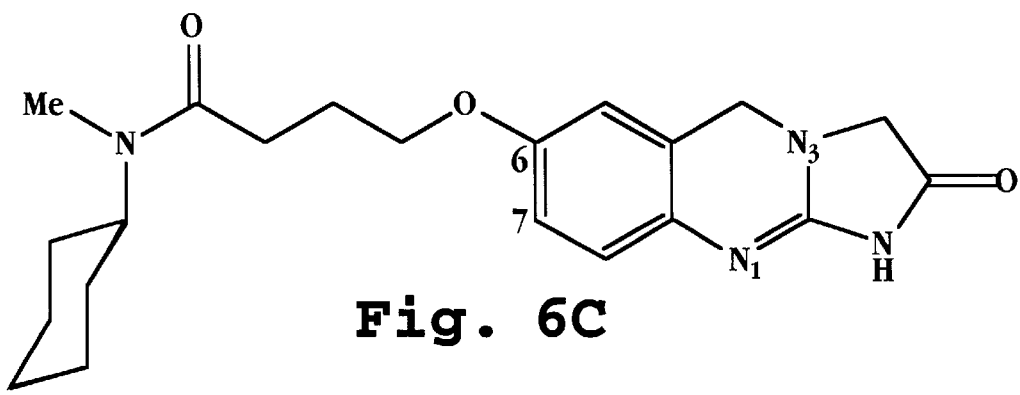
FIG. 6C shows the structure of lixazinone.
Figure 6D:
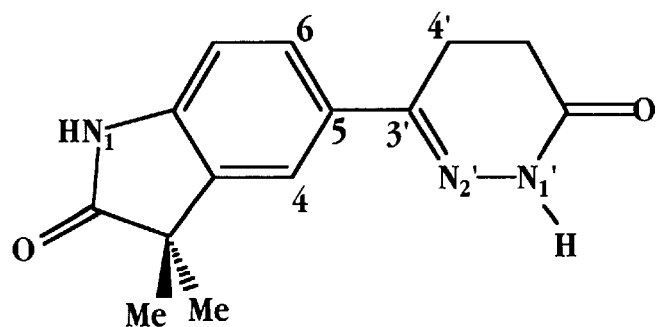
FIG. 6D shows the structure of indolidan.

Thus, the effects of these selective inhibitors differed markedly from the previously published (Dekel, et al., 1988; Dekel, et al., 1981) actions of the non-selective PDE inhibitor, IBMX. While IBMX consistently inhibited the maturation of isolated and follicle-enclosed oocytes as long as it was present in the culture medium, removal of IBMX from follicle-enclosed oocyte cultures revealed its ability to trigger the resumption of meiosis, like rolipram. Conversely, removal of milrinone or cilostamide, did not result in GVBD. These results are summarized in FIG. 5.

While not wishing to be bound by any particular mechanism, the studies described herein are consistent with the granulosa-cumulus cell compartment containing rolipram-sensitive type 4 PDEs (Conti, et al., 1984). The oocyte, by contrast, appears to contain type 3 PDEs, since milrinone and cilostamide inhibit both the spontaneous maturation of isolated oocytes as well as the LH-hCG-induced maturation of follicle-enclosed oocytes.

The nonselective inhibitor IBMX prevents the resumption of oocyte maturation by increasing granulosa cell cAMP levels (Tsafriri and Dekel, 1994) and by blocking oocyte PDE. Removal of IBMX in the two-step incubation model allows oocyte maturation to progress due to the initial rise in cAMP in the granulosa cell compartment followed by a decline in oocyte cAMP levels by local PDEs.

Finally, rolipram, which inhibits only type 4 PDEs which are localized primarily in the somatic compartment of the follicle, does not inhibit spontaneous and gonadotropin induced maturation of oocytes because it does not affect degradation of oocyte cAMP by its type 3 PDE. Conversely, rolipram can induce the maturation of follicle-enclosed oocytes by increasing cAMP levels in the somatic cell compartment. This conclusion is supported by the in situ hybridization studies in Example 3, showing PDE3B mRNA expressed in oocytes and PDE4 mRNA expressed in somatic cells of the ovary.

VII. Clinical Use of Type 3 PDE Inhibitors

The invention includes in one aspect a method of contraception by prevention of maturation of the oocyte. The method includes delivering to the ovaries of a female subject, a pharmaceutically-effective dose of a PDE3-specific inhibitor at midcycle.

A. Formulation and Administration of Pharmaceutical Compositions

Although any mode of administration may be used, so long as it provides sufficient concentration (pharmaceutically effective concentration) of compound to the ovary, it can be appreciated that certain modes of administration will be preferred in the treatment method. In particular, the compound or compounds are preferably administered in a manner that is amenable to convenient self-administration by the patient. Such modes include oral administration, nasal insufflation or intravaginal insertion. The relative pharmacokinetics of these modes of administration are known in the art. Other modes which may be employed include parenteral injection, such as intravenous or subcutaneous injection, as well as implantable devices which release the selected PDE3-specific inhibitor at selected times, transdermal delivery devices (e.g., "patch" application) and the like.

A preferred mode of administration is oral administration, since most of the PDE3-specific inhibitors can be absorbed in the digestive tract. In general, a pharmaceutically-effective amount of a PDE3-specific inhibitor or inhibitors, such as one or more of the inhibitors named in section IV above, and shown in FIGS. 6A–D and 7A–B is combined with a suitable additive, carrier and/or excipient in order to facilitate effective oral administration of the composition. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically usually used in the manufacture of medical preparations.

Liquid compositions can be prepared by dissolving or dispersing the compounds (about 0.5% to about 20%), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

In another preferred embodiment, the PDE3-specific inhibitor will be formulated in an intravaginal suppository insert having slow release properties, such as are afforded by the formulation described in U.S. Pat. No. 5,116,619, incorporated herein by reference. This formulation, which includes, in addition to the active ingredient, about 65–85% lactose, 2–4% starch paste, 2–4% corn starch and 0.4–0.6% magnesium stearate, allows for prolonged release of active ingredient over 48–72 hours. It can be appreciated that such a suppository formulation can be dispensed for alternate night self-administration, during the pre-ovulation and ovulation period determined according to the practitioner's understanding of the particular patient's ovulatory cycle and the principles taught herein.

An injectable composition for parenteral administration will typically contain a PDE3-specific inhibitor or an acceptable salt thereof in a suitable IV solution, such as sterile physiological salt solution. The composition may also formulated as a suspension in a lipid or phospholipid, in a liposomal suspension, or in an aqueous emulsion.

It will be appreciated that pharmaceutical compositions of the present invention may include additional active ingredient(s) effective to maintain elevated cAMP levels in the oocyte, e.g., activator(s) of type I protein kinase A (PKA).

B. Dosage

The dosage of a PDE3-specific inhibitor required to prevent oocyte maturation will depend on the specific compound and the route of administration, as described below. Generally, an effective dosage will be a dosage that provides in the ovary a concentration that is equivalent to a concentration of cilostamide or milrinone of about 1–10 $\mu$g/ml. This concentration can be achieved, e.g., by administering a dose of 1–100 mg/kg of compound once or twice per day. For specific compounds listed herein, further guidance to effective dosages can be obtained from the manufacturers' recommended dosages, or from the literature sources cited herein (C. f., Table 1), which are incorporated herein by reference.

The dose is determined in part based on the pharmacokinetics of the PDE3-specific inhibitor employed using standard pharmacokinetics principles known in the art.

Methods for preparing such dosages are known or will be apparent to those skilled in the art; for example, see *REMINGTON'S PHARMACEUTICAL SCIENCES* (1980). The composition to be administered will contain a quantity of the selected PDE3-specific inhibitor in a pharmaceutically effective amount for effecting contraception in the subject in need of contraception.

C. Timing of Delivery

According to the method of the invention, a PDE3-specific inhibitor is delivered to the ovary during a time period encompassing approximately 12 hours prior to the LH surge through at least about 48 hours after the surge. Accordingly, the drug is delivered to the ovary over a period of about 4–5 days at midcycle coincident with the LH surge.

Figure 8:
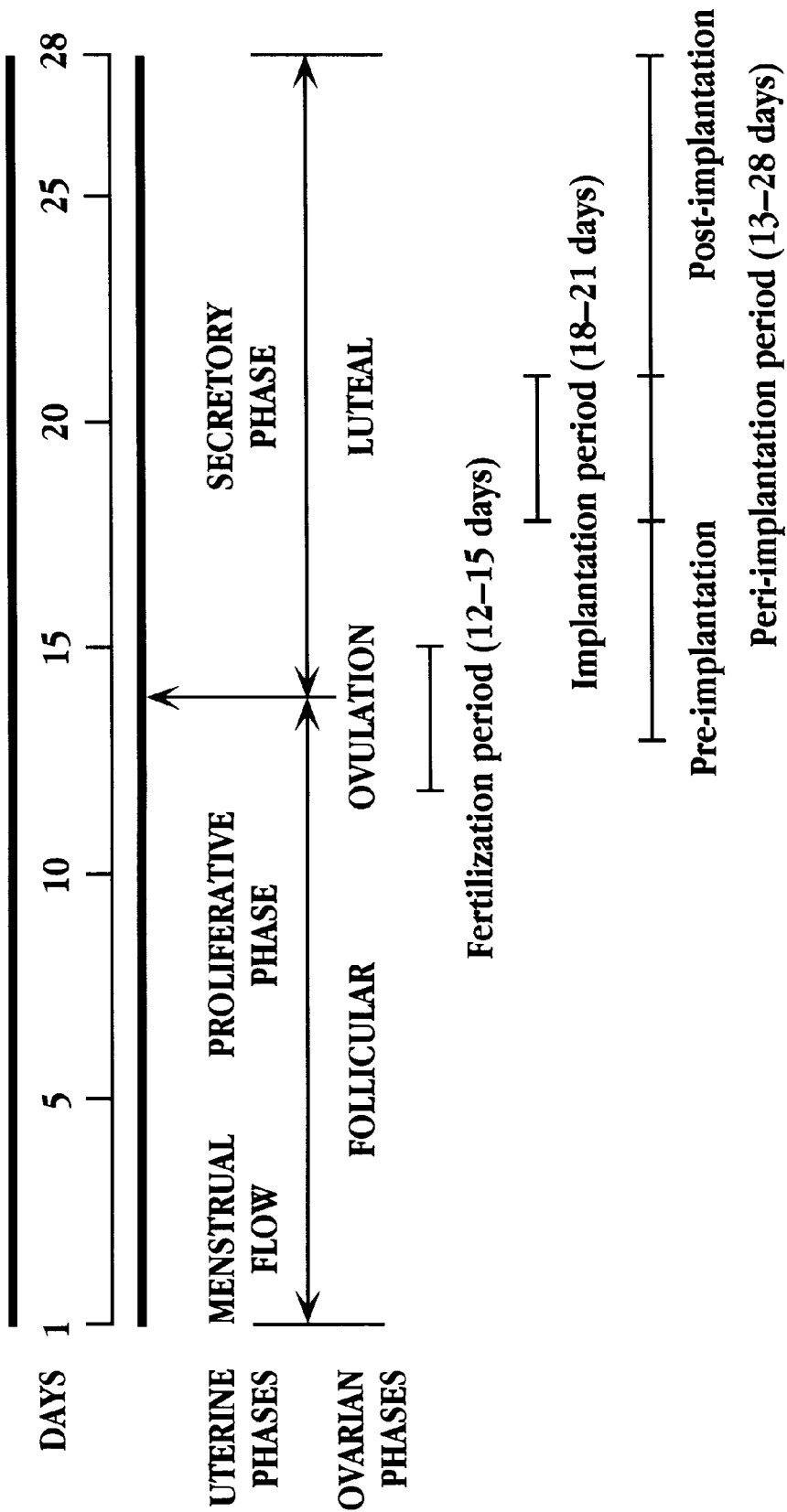
FIG. 8 is a schematic description of the human female ovarian cycle.

FIG. 8 shows a temporal depiction of the human menstrual cycle, in which day 1 indicates initiation of menstrual flow. Generally, ovulation occurs at about day 14 of the cycle, as depicted; however, this may vary considerably in and among individual women. Ovulation typically occurs just subsequent to a surge of LH and FSH levels in serum. These and other hormonal or physiological measures of ovulation may be measured according to standard methods known in the art.

For convenience, administration of the PDE3-specific inhibitor may be initiated one week after start of the ovarian cycle (i.e., one week after initiation of menstrual flow), and may be continued for up to two and one half weeks thereafter. Such a treatment regiment may be devised by providing, e.g., a set (e.g., container) of numbered pills to be taken at a rate of one pill per day, where a new set of pills is started on the day of initiation of menstrual flow, and where only pills from approximately pill number 7 to pill number 25 contain the PDE3-specific inhibitor. PDE3-specific inhibitors having no undesirable side effects may be taken continuously, avoiding the need for determining cycle timing.

VIII. Advantages and Applications

An advantage of the strategy described is that oocyte function is blocked without interference with the reproductive hormonal milieu and the normal menstrual cycle. Thus, because the estrous cycle and ovulation is not affected, the hypothalamic-pituitary-ovarian axis should not be altered during PDE3 inhibitor administration in vivo. This is considered to be an important advantage over the conventional steroid oral contraceptive. In addition, since final oocyte maturation occurs during a period of 12–24 hrs before ovulation, administration of the drug may be restricted to a relatively short period at around the midpoint of the menstrual cycle as described herein.

Since type 3 PDEs are also expressed during male gametogenesis at the end of meiosis, it is contemplated that PDE3 inhibitors can be used to manipulate male gametogenesis and thus alter fertility in the male.

The following examples illustrate but in no way are intended to limit the present invention.

MATERIALS AND METHODS

Unless otherwise indicated, chemicals were purchased from Sigma (St. Louis, Mo.) or United States Biochemical (Cleveland, Ohio).

A. Buffers

Phosphate-buffered saline (PBS)

10× stock solution, 1 liter:

80 g NaCl 2 g KCl 11.5 g $Na_2HPO4-7H_2O$ 2 g $KH_2PO_4$

Working solution, pH 7.3:

137 mM NaCl 2.7 mM KCl 4.3 mM $Na_2HPO_4-7H_2O$ 1.4 mM $KH_2PO_4$

B. Animals

Rats were obtained either from the Wistar-derived colony at the Department of Hormone Research (Weizmann Institute of Science, Rehovot, Israel) or from Simonsen Laboratories (Sprague-Dawley rats; Gilroy, Calif.). Animals were provided with water and rat chow ad libitum and housed in air-conditioned rooms illuminated for 14 hr/day. The results obtained using animals from both sources were indistinguishable and therefore pooled.

C. Culture Media and Inhibitors

Oocytes and follicles were cultured in Leibovitz's L-15 medium (L-15, GIBCO/BRL Life Technologies, Grand Island, N.Y.), supplemented with 5% fetal bovine serum (GIBCO or Sera-Lab, Crawley Down, England), penicillin (100 units/ml) and streptomycin (100 μg/ml; GIBCO). The PDE inhibitor IBMX was obtained from Sigma Chemical Co. (St. Louis, Mo.); rolipram and milrinone were obtained from Syntex Corp. (Palo Alto, Calif.); and cilostamide was obtained from Dr. I Hidaka (Nagoya University, Japan); the drug is also available from Otsuka Pharmaceutical Co., Ltd., Tokushima, Japan. The PDE inhibitors were kept as 10 mM stock solutions in dimethyl sulfoxide, and were diluted as indicated in the medium and added at the start of the culture in indicated experiments.

D. Oocyte Collection and Culture

Immature rats were injected with 10 IU equine chorionic gonadotropin (eCG) between 0900 0930 h on day 25–26 of age in order to enhance multiple follicular development. The animals were killed 48–52 h later by cervical dislocation. Oocytes were collected by puncturing the largest ovarian follicles under a dissecting microscope with a 25 G needle and exerting gentle pressure.

Twenty five to fifty oocytes, within their attached cumulus cell mass (termed "isolated oocytes"), were cultured in organ culture dishes (Falcon, Cockeysville, Md.) for 6 h in 1 ml of control or test media, as indicated in the Examples. Oocytes from 3 rats were pooled and distributed into at least 3 different dishes. The oocytes were collected into a medium containing IBMX (200 μM) and washed twice when transferred to the test medium. To confirm a direct action of cilostamide or milrinone on the oocyte, cumulus cells were removed by passage through a series of micropipettes after preincubation with collagenase (termed "denuded oocytes") as described by Piontkewitz and Dekel, 1993.

E. Follicle Culture

Immature Sprague-Dawley rats treated two days earlier with 10 IU eCG or mature rats that had shown two consecutive four-day cycles immediately before the experiment were sacrificed on the morning of the day of proestrus by cervical dislocation. Preovulatory follicles were excised under a dissection microscope as previously described (mature rats: Tsafriri, et al., 1972; immature rats: Dekel, et al., 1984). The follicles (7–15 per vial) were cultured for 24 h in control medium, in LH (5 μg/ml)-containing medium alone, or in LH-containing medium in combination with the indicated PDE inhibitors at the indicated doses. The vials were flushed at the start of the culture with $O_2/N_2$ (1/1), closed tightly and gently shaken during the culture.

A two-stage culture system was employed to test whether any of the PDE inhibitors was capable of inducing the resumption of meiosis in follicle-enclosed oocytes. This consisted of an initial culture period of 18 h with PDE inhibitors, followed (after a thorough washing in control medium) by an additional 6 h culture in control medium without the inhibitors.

F. Examination of Oocytes

Isolated oocytes were collected at the end of the 6 h culture period under a dissecting microscope. Follicle-enclosed oocytes were released after 24 h of culture by a small incision of follicle wall and collected. The meiotic stage of the oocytes was determined by examining them using Nomarski interference microscopy (Carl Zeiss Inc.) or by Hoffman modulation contrast (Nikon Corp.). Oocytes with a clear nuclear membrane (germinal vesicle; GV) or an intact nucleolus were classified as immature; those that did not show any nuclear structures, indicating that they have undergone germinal vesicle breakdown (GVBD), were classified as mature (Tsafriri and Kraicer, 1972). The standard error and statistical significance were calculated according to Ott (1988).

G. Probes used for In Situ Hybridization

PDE3A and PDE3B cDNA probes were generated by polymerase chain reaction (PCR; Mullis, 1987; Mullis, et al., 1987) using primers based on published sequences (Taira, et al., 1993). Primer A (5' TTTCTCGCCCAGAATA-CAAC 3'; SEQ ID NO:1) corresponds to bases 2598–2617 of rat PDE3A, while primer B (5' TTTTGCTAGTTGAG-GAGAAG 3'; SEQ ID NO:2) is complementary to bases 2949–2968 of rat PDE3A sequence. Primers C (5' CGTG-GATCCACGGCCGATTCCTGGCCTC 3'; SEQ ID NO:3) and D (5' CAATTCAAGCTTCTTGATAGCCTGGATTTG 3'; SEQ ID NO:4) correspond to bases 2310–2325 and 3343–3363, respectively, of the sequence of rat PDE3B.

PDE3A and PDE3B fragments were amplified from rat oocytes and rat heart cDNA, respectively. The amplified fragments were subcloned either by blunt end ligation (PDE3A fragment) or by ligation after BamH1-Hind3 digestion (PDE3B fragment) into "pBlueScript" (Stratagene, LaJolla, Calif.). The identity of the amplified fragments was confirmed by restriction enzyme digestion and sequencing.

Of the four PDE4 genes, PDE4B and PDE4D probes were chosen because they are the most abundant mRNAs in the ovary. The cDNAs for PDE4D and PDE4B, previously obtained by a screening of testis and Sertoli cell libraries (Swinnen, et al., 1989), were inserted into the EcoRI site of the "pBlueScript" polylinker. They were then linearized with a restriction enzyme at the 3' end of the mRNA to allow generation of 300 bp antisense probes using standard methods.

H. In situ Hybridization

Rat ovaries were dissected and fixed at 4° C. for 6 h in phosphate buffered 4% paraformaldehyde (pH 7.4) followed by immersion in 0.5 M sucrose in PBS overnight. Twelve-micron thick cryostat sections were mounted on slides coated with poly-L-lysine, fixed in 4% paraformaldehyde and stored at −70° C. for up to 1 month. Hybridization and washing of cryosections of rat ovaries were adapted from previously described methods (Chun, et al., 1993). The antisense and sense probes for the different PDEs were labeled with [$^{35}$S]UTP (1,000 Ci/mmol; NEN DuPont, Boston Mass.). The sections were hybridized under coverslips overnight at 50° C. in 50% formamide, 300 mM NaCl, 10 mM Tris-HCl (pH 8.0), 5 mM EDTA, 1× Denhardt's solution, 1 mg/ml yeast tRNA, and 10% dextran sulfate. After RNAse (25 μg/ml) treatment, slides were washed to a final stringency of 0.1 SSC at room temperature. After 2–3 weeks of exposure to NTB2 emulsion (Eastman Kodak, Rochester, N.Y.), sections were developed, counterstained, and mounted with "PERMOUNT" (Fisher Scientific, Fair Lawn, N.J.) for observation with bright and dark filed illumination using a Nikon Mikrophot-FXA microscope.

EXAMPLE 1

Inhibition of Maturation of Isolated Oocytes by Type-Selective PDE Inhibitors

The effects of several PDE inhibitors on spontaneous maturation of isolated oocytes, obtained 48 hours after eCG-stimulation of immature rats, were assayed by quantification of GVBD as described in the Materials and Methods. The results are shown in FIG. 1. Mean ± standard error of the mean (SEM) are indicated; when not shown, the SEM is smaller than the character used to represent the mean. The number of oocytes examined is given for each time-point in the figure or provided in parentheses in the written description of the experiment.

The spontaneous maturation of rat oocytes (72.9% GVBD; n=312) was blocked in a dose dependent manner by the non-specific PDE inhibitor IBMX, as well as by specific inhibitors of the type 3 PDEs—milrinone and cilostamide. Cilostamide was more effective with an apparent $ED_{50}$ of <1 μM as compared to milrinone ($ED_{50}$ of 5 μM).

A two-stage culture was employed to rule out any possible nonspecific toxic effects of milrinone and cilostamide: Following an initial 3 h culture with IBMX (200 μM), milrinone (10 μM) or cilostamide (10 μM), the cultures were washed and transferred to a control medium for overnight culture. This procedure resulted in complete reversal of the inhibitory effects of these drugs on spontaneous GVBD (96 [n=101], 95.2 [167] and 100% [106] GVBD, respectively, as compared to 95.9% [73] in control medium).

Direct action of the type 3 PDE inhibitors on the oocytes was further ascertained by using oocytes denuded from their cumulus cells. Cilostamide (10 μM) reduced GVBD to 20.6±3.9% (n=107) whereas milrinone reduced GVBD to 19.4±4.7% (n=67), as compared to 81.7±4.9% (n=60) GVBD in denuded oocytes cultured without any inhibitor. By contrast, rolipram, the specific inhibitor of type 4 PDEs, did not affect the spontaneous maturation, which proceeded undisturbed in its presence, even at the high dose of 500 μM (FIG. 1).

EXAMPLE 2

Inhibition of Maturation of Follicle-Enclosed Oocytes by Type-Selective PDE Inhibitors The effects of the PDE inhibitors IBMX, cilostamide (C), milrinone (M) and rolipram (R) on the maturation of follicle-enclosed oocytes were assayed and analyzed as described above. The results are shown in FIGS. 2A and 2B.

Figure 2A:
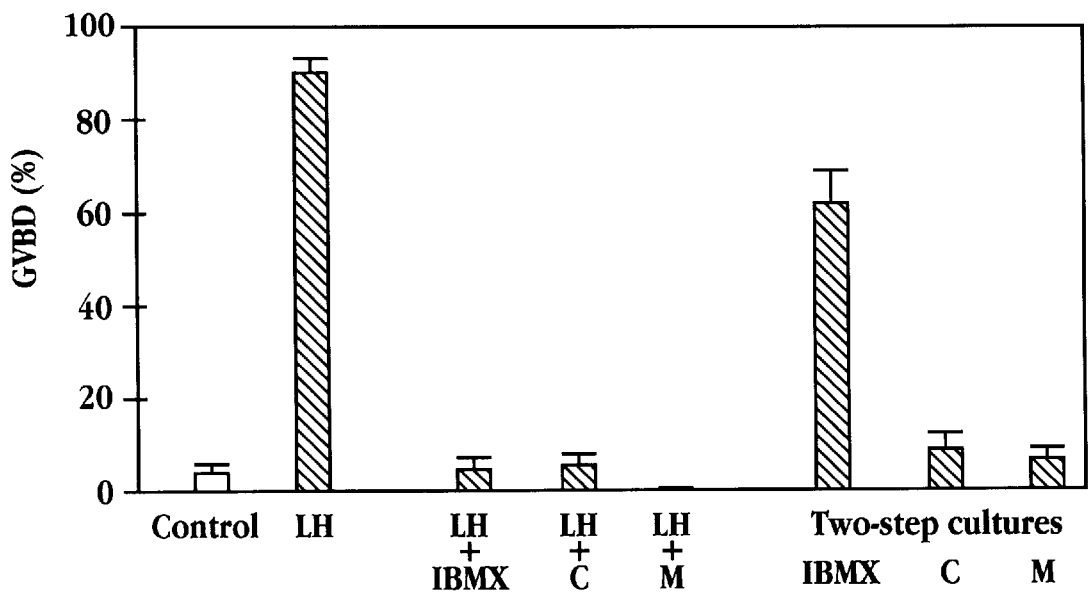
FIG. 2A shows a plot of the % GVBD in follicle-enclosed oocytes in control and LH-stimulated cultures containing different combinations of PDE inhibitors IBMX, milrinone (M), and cilostamide (C).

FIG. 2A shows the effects of IBMX (200 μM), cilostamide (C; 100 μM) and milrinone (M; 100 μM) on the maturation of follicle-enclosed oocytes. Note that each of these PDE inhibitors blocks LH-induced maturation when present throughout the culture period. In contrast, removal of IBMX and additional culture in control medium reveal the ability of IBMX to induce the resumption of meiosis. Cilostamide and milrinone are incapable of inducing the maturation of follicle-enclosed oocytes even in such two-step cultures.

In the follicle-enclosed oocyte model, the oocytes mature only in response to hormonal stimuli. LH/hCG is the physiological trigger of the resumption of meiosis and this response was blocked when the follicles were cultured in the presence of IBMX, milrinone or cilostamide. While IBMX was able to induce the resumption of meiosis in a two-step model (consisting of initial 18 h culture with the inhibitor, followed by additional 6 h culture in a control medium), milrinone and cilostamide did not elicit the resumption of maturation in this model.

Figure 2B:
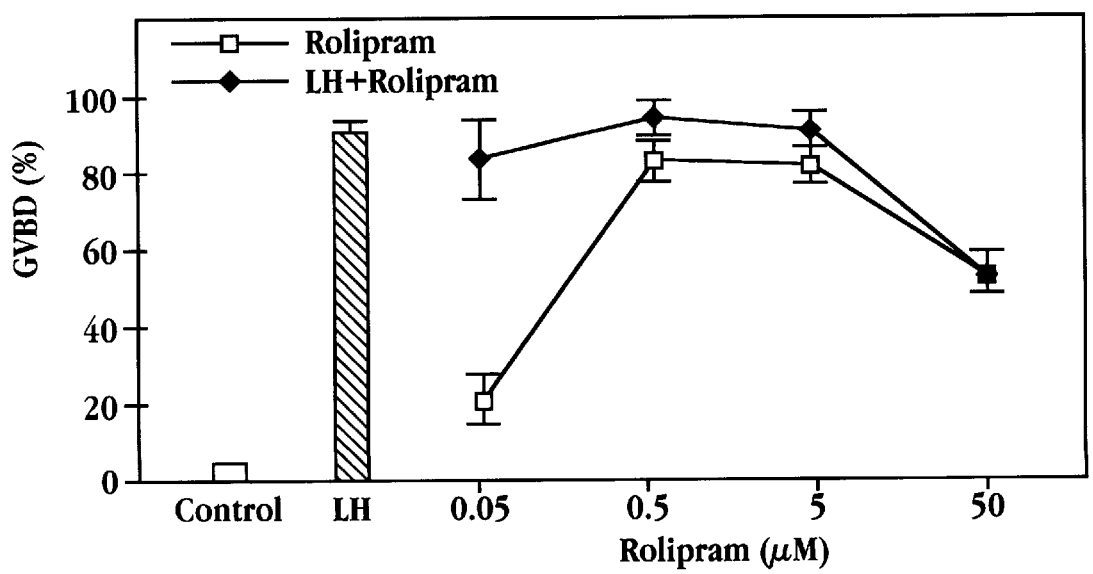
FIG. 2B shows plots of the % GVBD in follicle-enclosed oocytes in control and LH-stimulated cultures containing different concentrations of rolipram.

FIG. 2B shows induction of maturation in follicle-enclosed oocytes by rolipram. Preovulatory follicles were explanted from eCG-treated immature rats or cycling rats on the morning of proestrus and cultured overnight. Other details were as described in Example 1.

Treatment with increasing doses of rolipram (up to 5 μM), a selective inhibitor of type 4 PDE, did not inhibit the maturation of follicle-enclosed oocytes exposed to LH/hCG. In the absence of LH/hCG, rolipram stimulated the resumption of meiosis in follicles cultured without LH at doses between 0.05 and 5 μM. At concentrations of 50 μM or higher it partially inhibited LH/hCG-stimulated oocyte maturation, while still inducing the maturation of follicle-enclosed oocytes cultured in hormone-free medium. At these high concentrations, rolipram was less effective in stimulating GVBD. This may be due to the fact that at these higher doses rolipram inhibit PDE3 or that cAMP from granulosa cell compartment is transmitted to the oocyte compartment.

EXAMPLE 3

Expression of Type 3 and Type 4 PDE in Somatic and Germ Cell Compartment of the Follicle Based on PCR analyses of rat follicle cDNA confirming presence of PDE3 and PDE4 mRNA in this tissue, in situ hybridization experiments were performed on sections of ovaries of eCG-hCG treated animals to localize the expression of the PDE3 and PDE4 mRNAs in the somatic and germ cell compartments of the follicle. Exemplary results are shown in FIGS. 3A–F and 4A–F.

Figure 3A:
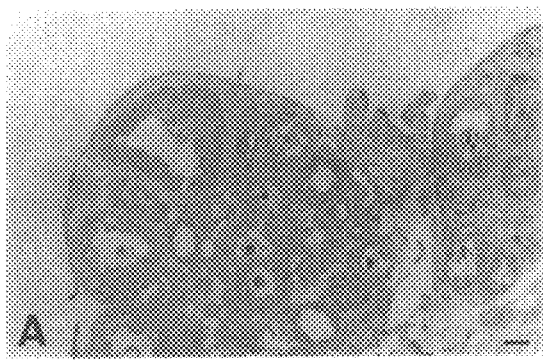
FIGS. 3A–F show in situ hybridization of a PDE3B-specific probe in ovarian and follicular tissue.
Figure 3B:
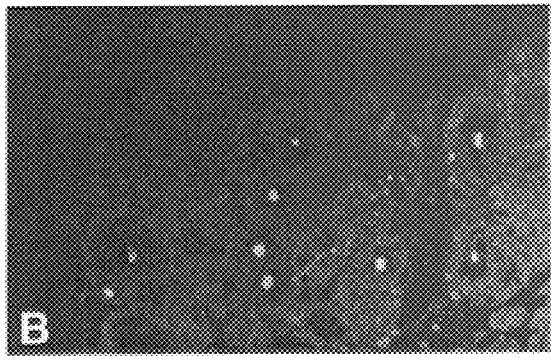
Figure 3C:
Figure 3D:
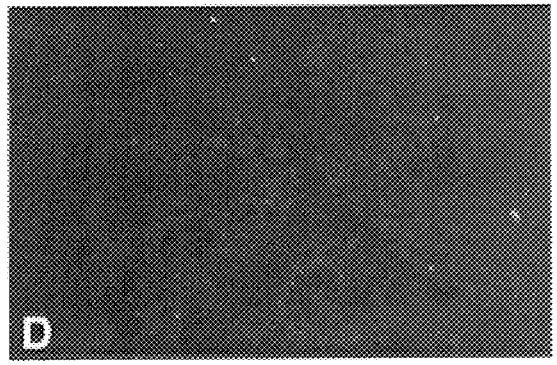
Figure 3E:
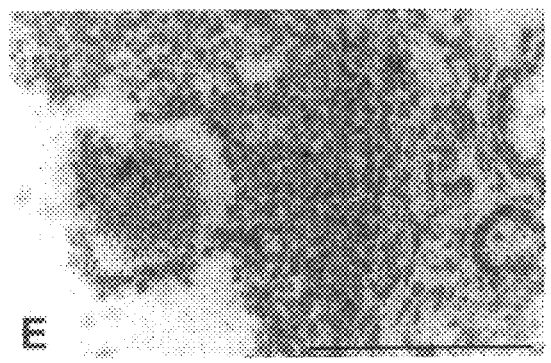
Figure 3F:
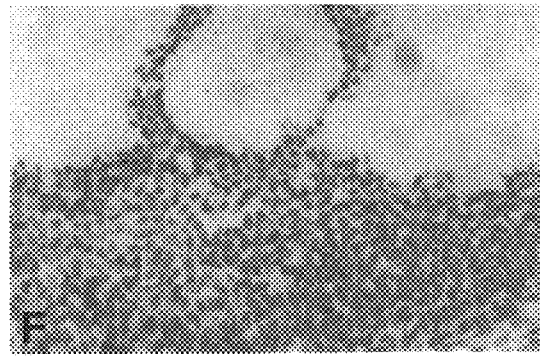
Figure 4A:
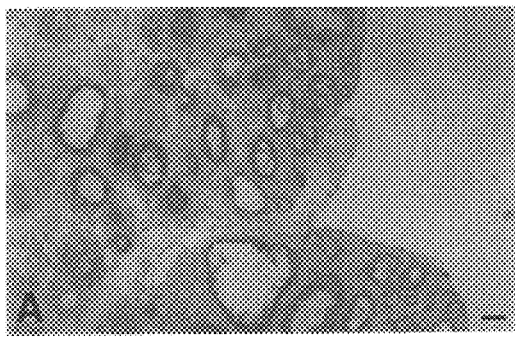
FIGS. 4A–F show in situ hybridization of a PDE4D-specific probe in ovarian and follicular tissue.
Figure 4B:
Figure 4C:
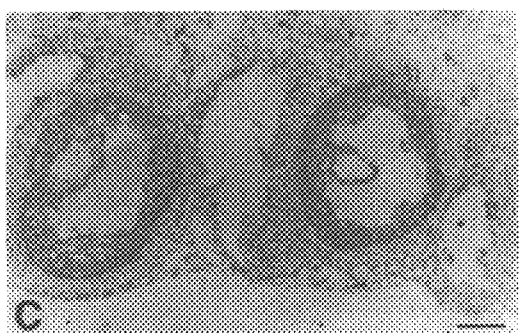
Figure 4D:
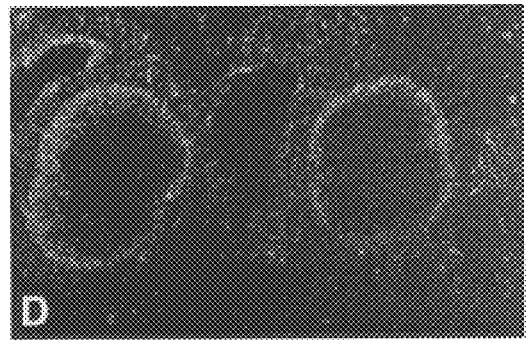
Figure 4E:
Figure 4F:
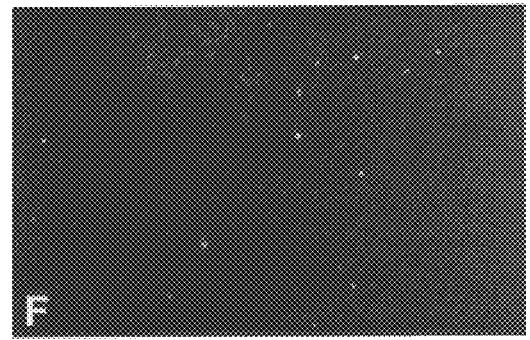

FIGS. 3A–F show ovarian and follicular expression using the PDE3B-specific probe. Expression was observed in the oocytes (FIGS. 3A, 3B, and 3E) but not in the sense controls or granulosa cells (FIGS. 3C, 3D, 3F). No specific signal was detected in the ovary using a probe specific for a different PDE3 isoform, PDE3A.

FIGS. 4A–F shows ovarian and follicular expression of PDE4D mRNA. In situ hybridization with the antisense probe revealed expression mainly in the mural granulosa cells of small and large antral follicles (FIGS. 4A, 4B, 4C, and 4D) while the sense controls (FIGS. 4E and 4F) are negative. Differences where also observed in the level of the signal during follicular maturation. While the strongest signal was observed in the large antral follicle, the signal from small immature follicles was only marginally above background. A PDE4B probe hybridized mostly to theca and interstitial cells. No signal was observed on oocytes with either PDE4 probe.

EXAMPLE 4

Inhibition of Oocyte Maturation In Vivo

PDE3 inhibitors (100 mg/kg) were administered daily by gavage to cycling mice. Treated animals had estrous cycles similar to the controls and spontaneous ovulation took place at the appropriate time, indicating that granulosa cell function was not impaired by this in vivo treatment. However, morphological examination of the ovulated oocytes from treated animals indicated that maturation had not occurred and the germinal vesicle was still present. These experiments demonstrate that inhibition of PDE3 prevents meiotic maturation of oocytes in vivo and causes the ovulation of immature and incompetent oocytes. Further, these findings support that inhibition of PDE3 is a useful method of blocking oocyte maturation in vivo, and confirm that this approach can be used as a non-hormonal method of contraception.

While the invention has been described with reference to specific methods and embodiments, it is appreciated that various modifications and changes may be made without departing from the invention.

It is claimed:

1. A method of contraception, comprising delivering to the ovaries of a female mammal a pharmaceutically-effective dose of a phosphodiesterase 3 (PDE3) specific inhibitor at midcycle.

2. The method of claim 1, wherein said PDE3-specific inhibitor is selected from the group consisting of milrinone, cilostamide, amrinone, enoximone, 3-(2H)-pyridazinone-4,5-dihydro-6-(4-(1H-imidazolyl) phenyl)-5-methyl monohydrochloride (CI-930), anagrelide, pimobendan, siguazodan (SKF-94836), lixazinone (RS-82856), imazodan (CI-914), indolidan (LY195115), quazinone, 5-(4-acetamidophenyl) pyrazin-2(1H) (SKF 94120), N-hydroxy-5,6-dimethyl-benzo(b)thiophene-2-carboximidamide (Org 30029), adibendan (BM 14,478), 3-amino-6-methyl-5-phenyl-1,2-dihydropyrid-2-on (APP 201-533), carbazeran, cilostazole, loprinone (E-1020), IPS-1251, nanterinone (UK-61260), pelrinone, 1,3-dihydro-4(4-methoxybenzoyl)-5-methyl-2H-imidazol-2-one (RMI 82249), 2-(4-hydroxy-phenyl)-5-(5-methyl-3-oxo-4,5-dihydo-2H-6-pyridazinyl) benzimidazole (pimobendan UD-CG 212), bemarinone (ORF-16,600), 4-ethyl-1,3-dihydro-5-(4-(2-methyl-1H-imidazol-1-yl) benzoyl)-2H-imidazol-2-one (CK-2130), motapizone, N-cyclohexyl-N-2-hydroxyethyl-4(6-(1,2-dihydro-2-oxoquinolyloxy))butyramide (OPC-3911), (R-6-chloro-1,5-dihydro-3-methylimidazo-(2,1-b) quinazolin-2(3H)-one) (Ro 13-6438), sulmazole, vesnarinone (OPC-8212), buquineran, 5-(4-cyanophenyl)-1,2-dihydro-6-methyl-2-oxopyridin-3-carbonitrile (DPN 205-734), (6RS)-6-methyl-5-(pyrid-4-yl)-3H,6H-1,3,4-thiadiazin-2-one (ICI-170777), isomazole (LY175326), 6-(4-(4-pyridyl)aminophenyl)-4,5-dihydro-3(2H)-pyridazinone (MCl-154), 7-(4-pyridyl)-5,6,7,8-tetrahydro-3(2H)-isoquinolinone (MS-857), 3,4-dihydro-6-(4-(4-oxo-4-phenylbutyl)-1-piperazinylcarbonyl)-2(1H)-quinolinone citrate (OPC-8490), piroximone (MDL 19205), 2-(2-chloro-4-(2,3,4,5-tetrahydro-3-oxo-6-pyridazinyl))-phenoxy-N-(2-(2-morpholinoethyl)-acetamide (RS-1893), saterinone, 4-methyl-5-(4-pyridinyl)-thiazole-2-carboxyamide (ZSY-39), 6-(p-(3-methylureido)phenyl)-3(2H)-pyridazinone (ICI 118233).

3. The method of claim 2, wherein said PDE3-specific inhibitor is milrinone.

4. The method of claim 2, wherein said PDE3-specific inhibitor is cilostamide.

5. The method of claim 2, wherein said PDE3-specific inhibitor is lixazinone.

6. The method of claim 2, wherein said PDE3-specific inhibitor is indolidan.

7. The method of claim 1, wherein said PDE3-specific inhibitor is delivered via oral administration.

8. The method of claim 1, wherein said PDE3-specific inhibitor is delivered via vaginal administration.

9. The method of claim 1, wherein said dose is between about 1 mg/kg and about 100 mg/kg per day.

10. The method of claim 1, wherein said female mammal is a rodent.

11. The method of claim 1, wherein said female mammal is a woman.

12. The method of claim 1, wherein said delivery at midcycle includes delivery over a period spanning from about 12 hours before the LH surge to about 48 hours after the LH surge.

13. The method of claim 1, wherein said delivery at midcycle includes delivery over a period spanning from about 7 days after start of the menstrual cycle to about 25 days after start of the menstrual cycle.

14. A contraceptive device for use in preventing oocyte maturation in a female mammal, comprising
   a vaginal insert, and
   compound release means in said insert for releasing a PDE3-specific inhibitor at a dose effective to prevent oocyte maturation.

15. The method of claim 1, wherein said PDE3-specific inhibitor is a pyridazinone derivative having the structure:

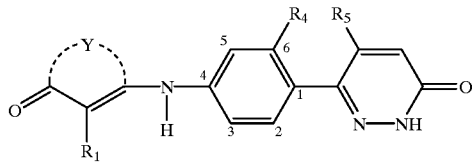

wherein Y represents $CH_2CH_2$, $CH_2CH_2CH_2$ or $C(CH_2)_2(CH_3)_2$; R1 is H, $CH_2$, or $CH_3$; and R4 and R5 are H, $CH_2CH_2$, or $OCH_2$.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: Primer A (xi) SEQUENCE DESCRIPTION: SEQ ID NO:1:

TTTCTCGCCC AGAATACAAC       20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (iii) HYPOTHETICAL: NO (iv) ANTI-SENSE: NO (vi) ORIGINAL SOURCE:
      (C) INDIVIDUAL ISOLATE: Primer B (xi) SEQUENCE DESCRIPTION: SEQ ID NO:2:

TTTTGCTAGT TGAGGAGAAG       20

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer C (xi) SEQUENCE DESCRIPTION: SEQ ID NO:3:

CGTGGATCCA CGGCCGATTC CTGGCCTC                    28

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: Primer D (xi) SEQUENCE DESCRIPTION: SEQ ID NO:4:

CAATTCAAGC TTCTTGATAG CCTGGATTTG                  30